(12) United States Patent
Mehta (10) Patent No.: US 9,449,380 B2
(45) Date of Patent: Sep. 20, 2016

(54) MEDICAL IMAGE QUALITY MONITORING AND IMPROVEMENT SYSTEM

(71) Applicant: Darshan Mehta, Gilberts, IL (US)

(72) Inventor: Darshan Mehta, Gilberts, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 267 days.

(21) Appl. No.: 13/766,007

(22) Filed: Feb. 13, 2013

(65) Prior Publication Data

US 2013/0251219 A1 Sep. 26, 2013

Related U.S. Application Data

(60) Provisional application No. 61/613,001, filed on Mar. 20, 2012.

(51) Int. Cl.
| | | |
|---|---|---|
| G06K 9/00 | (2006.01) | |
| G06T 7/00 | (2006.01) | |
| G06F 19/00 | (2011.01) | |

(52) U.S. Cl.
CPC .......... *G06T 7/0012* (2013.01); *G06F 19/321* (2013.01)

(58) Field of Classification Search
None
See application file for complete search history.

(56) References Cited

U.S. PATENT DOCUMENTS

| | | | |
|---|---|---|---|
| 5,986,662 A * | 11/1999 | Argiro et al. ................. 345/424 |
| 6,768,811 B2 * | 7/2004 | Dinstein et al. ............. 382/128 |
| 6,987,892 B2 * | 1/2006 | Edgar .......................... 382/254 |
| 7,187,790 B2 | 3/2007 | Sabol et al. |
| 7,426,567 B2 * | 9/2008 | Wortmann et al. .......... 709/231 |
| 7,602,987 B2 * | 10/2009 | Kuramoto ..................... 382/254 |
| 7,864,993 B2 * | 1/2011 | Maack et al. ................ 382/128 |
| 8,040,406 B2 * | 10/2011 | Enomoto ...................... 348/246 |
| 8,107,695 B2 * | 1/2012 | Wollenweber ............ G06T 7/20 382/107 |
| 8,333,508 B2 * | 12/2012 | Reiner .................... A61B 6/581 378/207 |
| 8,625,866 B2 * | 1/2014 | Hill et al. ..................... 382/128 |
| 8,879,807 B2 * | 11/2014 | Fram et al. ................... 382/128 |
| 9,092,727 B1 * | 7/2015 | Reicher |
| 9,138,163 B2 * | 9/2015 | Deitz .................. A61B 5/0555 |
| 2003/0039403 A1 * | 2/2003 | Robins ......................... 382/275 |
| 2004/0122787 A1 | 6/2004 | Avinash et al. |
| 2004/0122790 A1 | 6/2004 | Walker et al. |
| 2004/0218804 A1 | 11/2004 | Affleck et al. |
| 2011/0110572 A1 | 5/2011 | Guehring et al. |
| 2012/0141002 A1 | 6/2012 | Urbano et al. |
| 2012/0321168 A1 | 12/2012 | Deitz |

* cited by examiner

*Primary Examiner* — Nancy Bitar (57) ABSTRACT

A medical image quality reporting and monitoring system for use in a medical imaging system comprises a medical image computer including, a display processor, a display and a report generator. The display processor generates data representing an image for display including a user selectable image element enabling a user to identify at least one medical image as having an image quality deficiency. The display presents the image. The report generator, in response to detection of selection of the image element, identifying at least one medical reduced quality image as having an image quality deficiency, automatically generates a report. The report comprises, data representing an anonymized reduced quality image having the image quality deficiency, a time of acquisition of the reduced quality image and imaging system acquisition settings used in acquiring the reduced quality image.

15 Claims, 5 Drawing Sheets

MEDICAL IMAGE QUALITY MONITORING AND IMPROVEMENT SYSTEM

This is a non-provisional application of provisional application Ser. No. 61/613,001 filed Mar. 20, 2012, by D. Mehta.

FIELD OF THE INVENTION

This invention concerns a medical image quality reporting and monitoring system for automatically generating a report comprising, an anonymized reduced quality image having an image quality deficiency, a time of acquisition of the image and imaging system acquisition settings used in acquiring the image, in response to a determined image quality deficiency.

BACKGROUND OF THE INVENTION

In response to a user performing image acquisition and review using an angiography imaging system, a desired level of image quality may not be attained due to a variety of reasons such as incorrect use of image processing settings and sub-optimal performance of image processing methods or other software defects. Often such occurrences are sporadic or associated with a particular workflow performed by a particular user and expressed as a complaint and dissatisfaction to service personnel or image quality experts. Further investigation of such complaints takes substantial effort and resources (involving multiple visits to a reporting site to acquire data such as acquired image, image examination data sets, data indicating performed workflow and engineering logs, for example). A complaint may also be overlooked and may not get investigated due to a non-reproducible nature of a problem, leaving an imaging system user dissatisfied. A system according to invention principles addresses these deficiencies and related problems.

SUMMARY OF THE INVENTION

A system enables a user to express dissatisfaction with image quality outcome via simple button press on a patient table side UI, computer workstation or other displayed image and in response acquires relevant information for investigation and examination assessment without manual intervention of service personnel or image quality experts. A medical image quality reporting and monitoring system for use in a medical imaging system comprises a medical image computer including, a display processor, a display and a report generator. The display processor generates data representing an image for display including a user selectable image element enabling a user to identify at least one medical image as having an image quality deficiency. The display presents the image. The report generator, in response to detection of selection of the image element, identifying at least one medical reduced quality image as having an image quality deficiency, automatically generates a report. The report comprises, data representing an anonymized reduced quality image having the image quality deficiency, a time of acquisition of the reduced quality image and imaging system acquisition settings used in acquiring the reduced quality image.

DETAILED DESCRIPTION OF THE INVENTION

A system enables a user to express dissatisfaction with quality of an image acquisition outcome via simple button press on a patient table side user interface (UI), computer workstation or other displayed image and in response acquires relevant information for investigation and examination assessment without manual intervention of service personnel or image quality experts. In response to observing unsatisfactory image quality at the end of, or during, an image processing workflow using an angiography system, for example, a user is able to report an image quality problem via pressing a special button provided on a table side control, or other user interface display image on a workstation.

Figure 1:
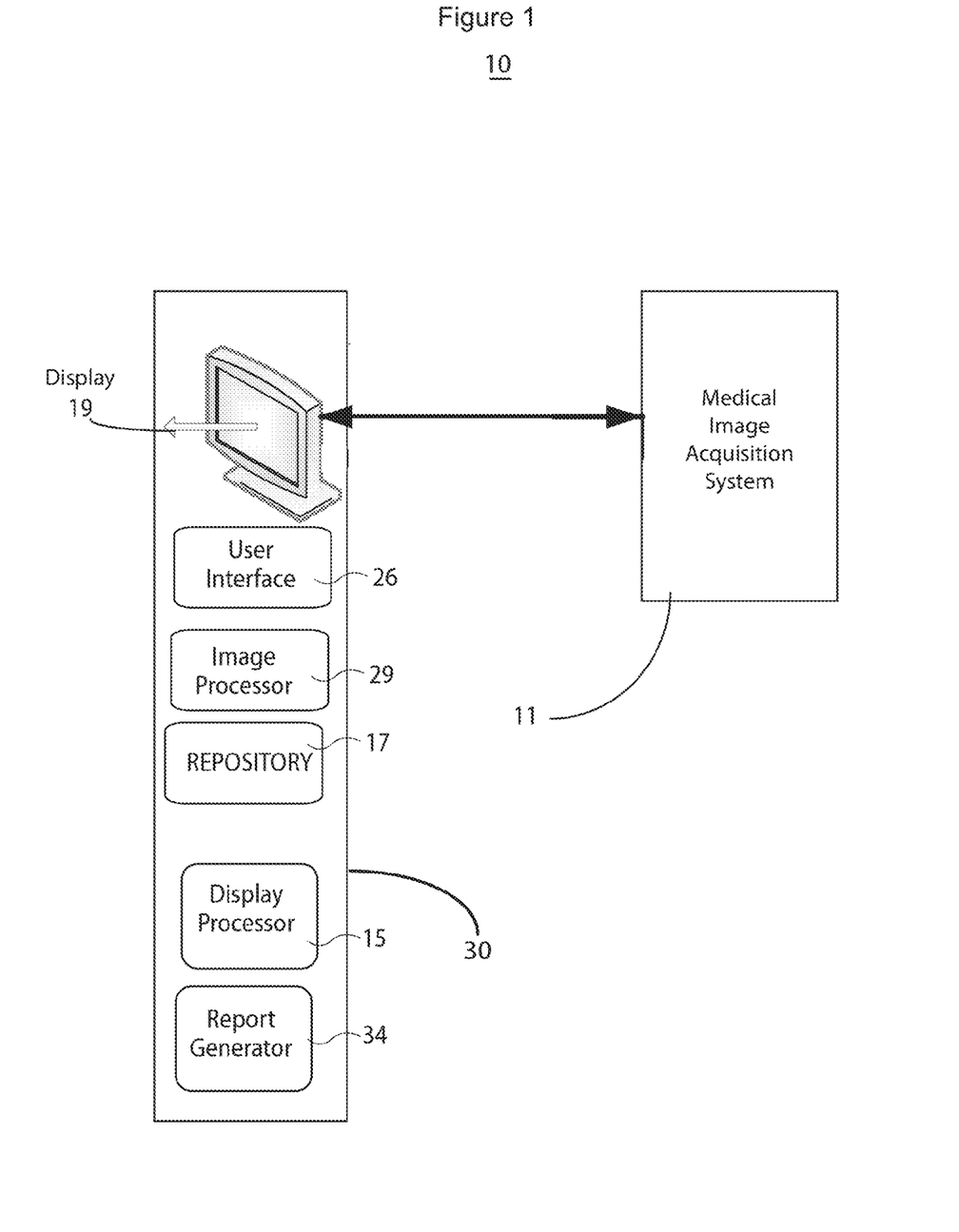
FIG. 1 shows a medical image quality reporting and monitoring system for use in a medical imaging system, according to invention principles.

FIG. 1 shows medical image quality reporting and monitoring system 10 for use in a medical imaging system. System 10 comprises image acquisition device 11 bidirectionally communicating with at least one medical image computer system, workstation, server or other processing device 30 including, display 19, repository 17, display processor 15, user interface 26, image processor 29 and report generator 34. Display processor 15 generates data representing an image for display including a user selectable image element enabling a user to identify at least one medical image as having an image quality deficiency. Display 19 presents the image and report generator 34, in response to detection of selection of the image element, identifying at least one medical reduced quality image as having an image quality deficiency, automatically generates a report. The report comprises data representing an anonymized reduced quality image having the image quality deficiency, a time of acquisition of the reduced quality image and imaging system acquisition settings used in acquiring the reduced quality image. The report also includes, a record of a sequence of user interface actions occurring preceding and related to acquisition of the reduced quality image, a problem description and system configuration settings and data representing multiple anonymized reduced quality images displayed on one or more display screens at the time of user selection of the image element. Repository 17 stores anonymized reduced quality images and associated generated reports and associated problem description information. Image processor 29 uses the settings for automatically acquiring and processing an image to provide a comparison image in response to detection of selection of the image element.

Figure 2:
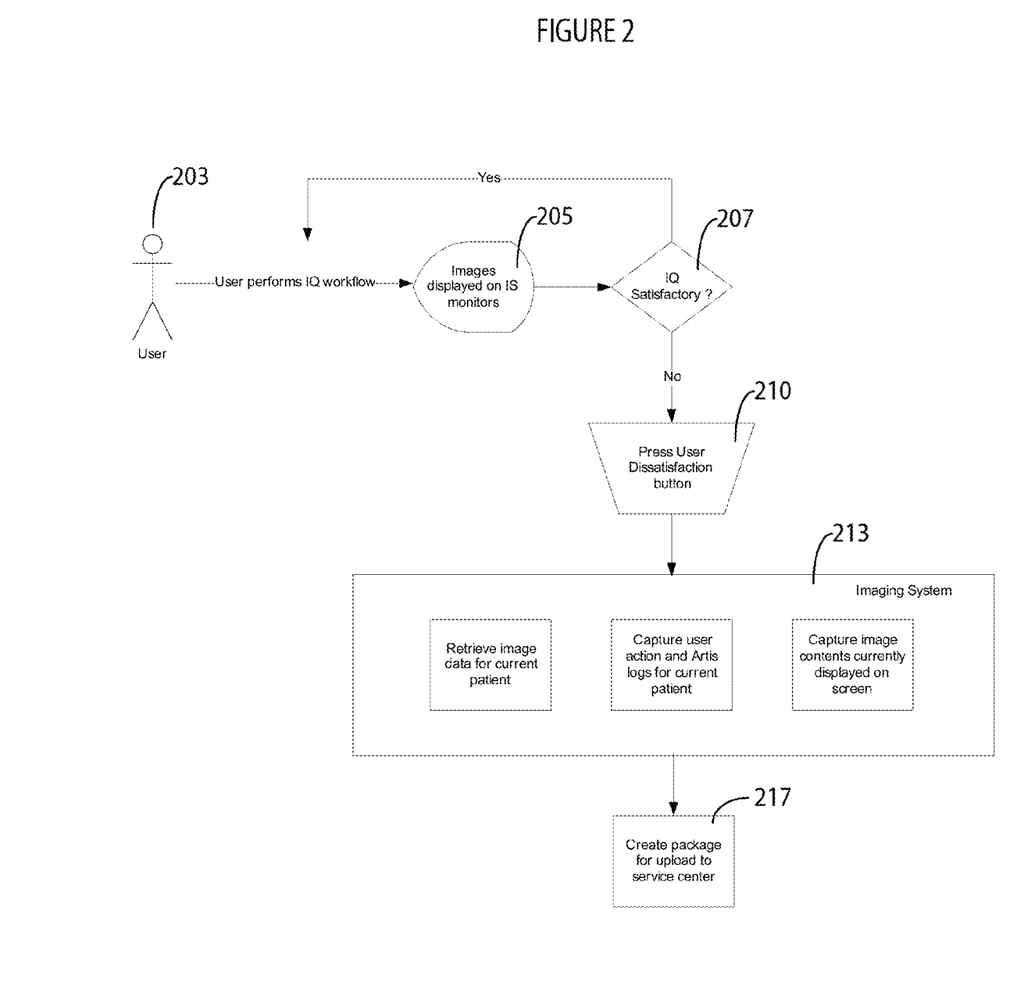
FIG. 2 shows a method for capturing user dissatisfaction and relevant information, according to invention principles.

FIG. 2 shows a method employed by system 10 (FIG. 1) for capturing user dissatisfaction and relevant information. User 203 initiates an image quality workflow when images are displayed on an imaging system monitor in step 205. The user in step 210 activates a dissatisfaction button in response to a determination an image is of reduced quality in step 207, otherwise steps 205 and 207 are iteratively repeated. In response to receiving an image quality deficiency report as a trigger from user activation of the dissatisfaction button, report generator 34 residing on the imaging system, in step 213, automatically, determines a time of acquisition and registered patient identifier associated with an image of deficient quality and generates a log record that contains UI action history, acquisition parameters, image quality assessment and problem description and system configuration parameters. Generator 34 anonymizes the image of deficient quality and captures images associated with a quality deficiency currently displayed on display 19 and provided by imaging system 11. Generator 34 also anonymizes problematic images and exports data representing the anonymized image data to a predetermined directory in repository 17 and in step 213 generates a record with data of step 213 and uploads it to a remote service centre or notifies service personnel assigned to a particular site.

System 10 also acquires feedback information concerning accuracy of certain image processing functions derived by training the image processing functions on a predetermined image data set. In response to detection of a failure in using an image processing function during processing of a particular dataset, an internal trigger is generated comprising a specific error code sent to the system which automatically generates a record with relevant data identifying the context, circumstances and nature of the failure and uploads the record to a service centre. The predetermined image data set is used to fine tune an image processing function and increase user satisfaction for a particular image processing feature. The system in one embodiment automatically identifies poor image quality or prompts a user that image quality may be deficient e.g. by comparison with template reference images of an anatomical region of interest (ROI) concerned or by detecting, common artifacts, banding, poor luminance range or monochrome areas, for example.

System 10 automatically determines a reason for poor image quality, e.g., by comparing settings and workflow steps for a particular procedure with template settings and workflow to identify incorrect settings or workflow steps and missing elements. In order to further improve user satisfaction with image quality, system 10 provides an image quality (IQ) analysis function. The imaging system supplies a user with multiple Image Quality profiles identified from a lookup table. Image quality profiles comprise a set of image processing parameters (e.g. settings which are a combination of organ program parameters and image quality configuration parameters) that are pre-validated to provide optimal image quality for an image processing function with a particular set of X-ray radiation detectors and type of image acquisition (e.g. workflow being executed by a user), for example.

Figure 3:
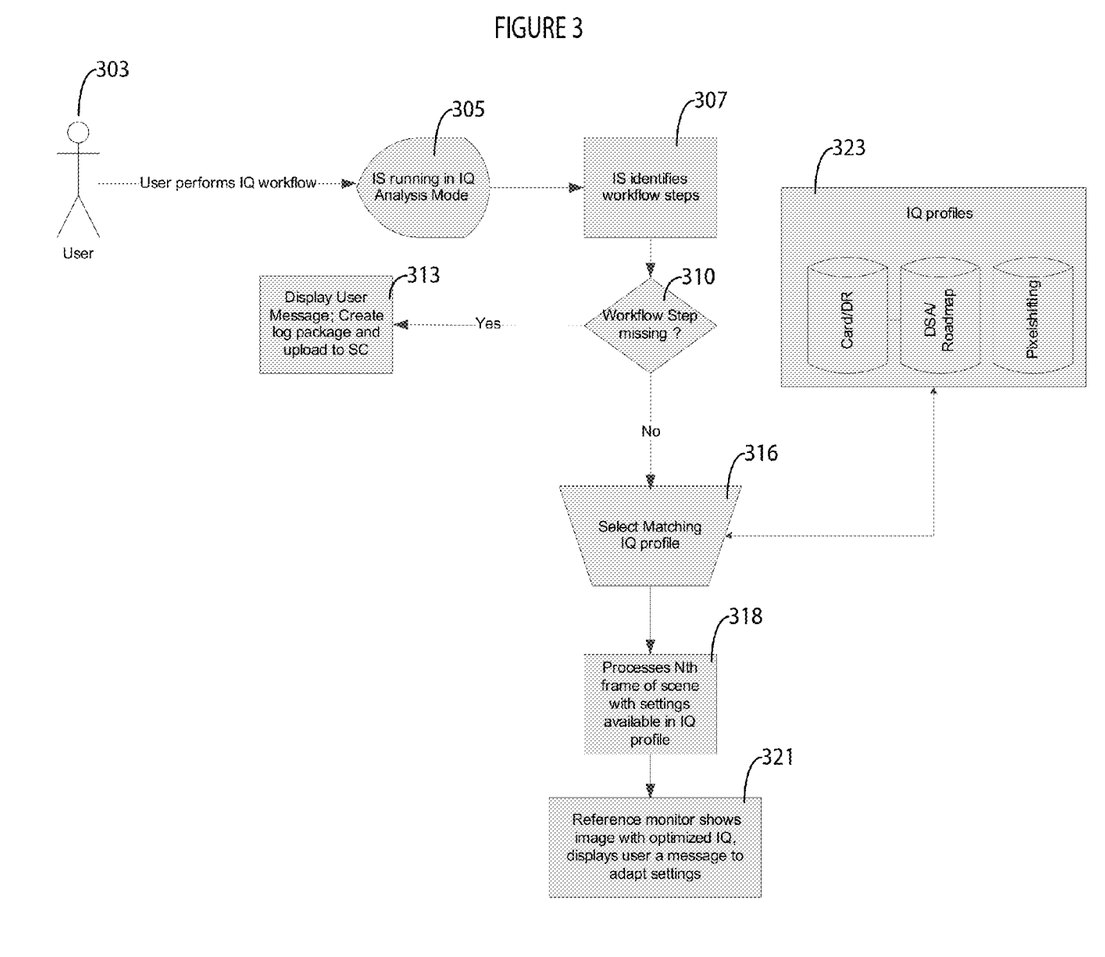
FIG. 3 shows a method for automatic detection and improvement of Image Quality, according to invention principles.

FIG. 3 shows a method employed by system 10 (FIG. 1) for automatic detection and improvement of Image Quality. In an IQ analysis function mode entered in step 305 in response to user 303 command, a user imaging system workflow is identified in step 307 by system 10 by parsing user actions. Report generator 34 in step 310 determines if a workflow step affecting image quality is omitted by comparing the workflow steps performed against a predetermined list of steps for an identified imaging function determined from a map associating identified user actions with imaging system operation functions. In step 313 in response to identifying that a workflow step affecting image quality is omitted, report generator 34 presents an alert message to the user on display 19 and generates a log record that contains UI action history, acquisition parameters, image quality assessment and problem description and system configuration parameters and communicates the generated report to a remote service centre and notifies service personnel assigned to a particular site.

In response to identifying that a workflow step affecting image quality is not omitted in step 310, report generator 34 in step 316 selects an image quality profile corresponding to the imaging function being performed as determined from the recorded user actions or from data acquired from a patient record or other user entered data identifying an imaging system function and procedure being performed. Report generator 34 selects the image quality profile from profiles 323 stored in repository 17. Identification and selection of a correct image quality profile is further achieved in step 318 by comparing the image processing parameters (e.g. settings) used in acquiring an image against corresponding pre-optimized settings in one or more profiles and upon finding significant deviation, system 10 processes an Nth frame of such images using settings in the available profile and displays the image on a reference monitor in step 321. A user is able to compare the image quality differences between an original image and an image acquired with predetermined optimized settings of a profile and is provided with an option to adapt current settings to match the ones in the optimized profile. Such profiles are user specific and cater to the needs and preferences of an individual specific workflow.

System 10 provides a user with multiple Image Quality profiles. A profile includes a set of image processing parameters (e.g. settings which are a combination of organ program parameters and image quality configuration parameters) that are pre-validated to provide optimal image quality for an image processing function with a particular set of X-ray radiation detectors and type of image acquisition and workflow being executed by a user. When system 10 operates in image quality analysis function mode, a user workflow is identified by the system by parsing and comparing user actions against predetermined sequences of user actions associated with predetermined imaging protocols and functions and in response to the comparison, system 10 selects a corresponding subset of image quality profiles. Further isolation of correct profiles is achieved by comparing image processing parameters (e.g. settings) against the ones indicated in pre-optimized image quality profiles and upon finding significant deviation, imaging system processes an acquired Nth image frame using settings in an identified profile and displays the image on display 19. A user is able to compare image quality differences and to adapt current settings to match one in a profile.

In order to improve user satisfaction concerning image quality, system 10 provides a quality analysis function that presents a user with multiple options in response to determining a resultant image quality by analyzing a user imaging system operation workflow. In one embodiment system 10 selects pre-validated optimal image quality settings in response to user predetermined preferences for speed of acquisition and processing versus image quality. When a user performs a fluoroscopic or other image acquisition on an angiography imaging system, different subsystems of system 10 track user actions including selection of button push, selection of type of acquisition from table side control, table and stand movements and records this information in a file which is saved in repository 17. The imaging system uses this information to learn the type of acquisition and set of image processing parameters that are used to perform a particular image acquisition.

Figure 4:
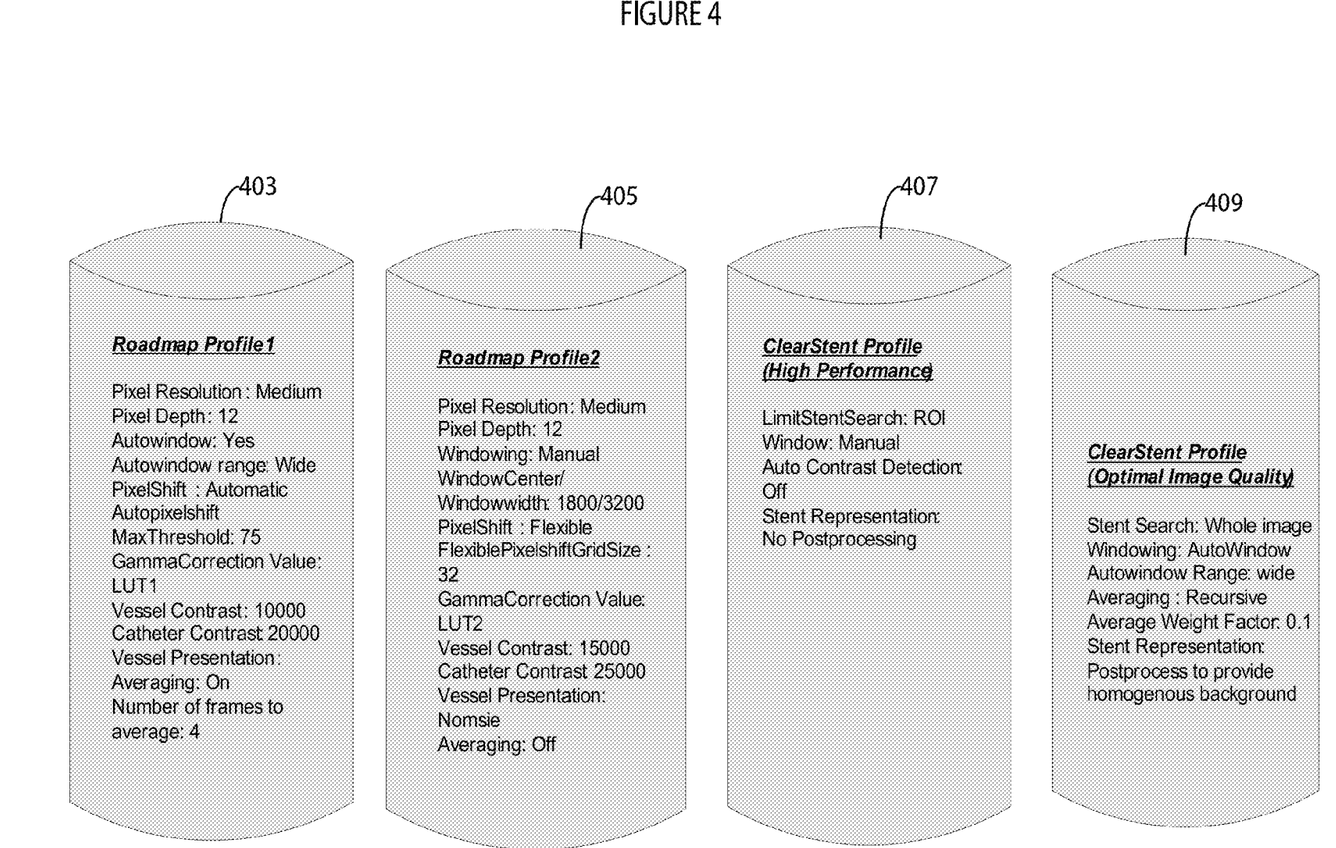
FIG. 4 shows Quality profiles classified based on type of image acquisition, according to invention principles.

FIG. 4 shows different Quality profiles 403, 405, 407 and 409 classified based on type of image acquisition that are maintained by system 10 in repository 17. These profiles are pre-validated to provide optimal image quality for a type of image acquisition or an imaging procedure. For example, where a user is performing a Roadmap acquisition of image vasculature (profile 403), the imaging system uses a log parsing function to identify the type of acquisition and load a corresponding image quality profile. The imaging system cross checks predetermined quality template roadmap settings in profile 403 against the settings used for a current image acquisition by comparing use of a pixel shifting algorithm (automatic versus Flexible), autopixelshift threshold, vessel representation, number of frames used to perform mask averaging for noise reduction, pixel resolution, pixel depth, autowindow activation and range, Gamma correction value, vessel contrast, catheter contrast, for example. Based on the analysis of the deviation in current image acquisition settings from those of profile 403, the imaging system prompts a user to initiate a quality analysis function. In this mode, system 10 processes an Nth frame from an acquired sequence of images with recommended settings from profile 403 and displays the processed image on display 19 enabling user side by side comparison with the original acquired image. A user is able to accept the quality function settings and make quality profile 403 an active profile for consecutive image acquisitions of the same type.

In another embodiment, predetermined quality template image acquisition settings comprising a quality profile, are selected as the setting profile to be used based on user preference of performance (speed) versus image quality. For resource intensive image processing, speed may be improved at the expense of image quality and vice versa. A log parsing system in report generator 34 is used to identify type of acquisition. Generator 34 learns a type of image acquisition being used and loads corresponding image processing profiles (e.g. clearstent profile 409). In response to comparison of current settings of clearstent acquisition parameters against settings in profile 409, generator 34 prompts a user to initiate a quality analysis function. Report generator 34 re-processes an image with stent detection using profile 409 settings and provides the re-processed image on display 19. A user may accept the profile 409 settings as the active image acquisition and post-processing settings for consecutive clearstent image acquisitions.

Optimized profile settings are obtained using a lookup table in repository 17 associating in different columns, different types of image processing function being performed with type of image acquisition, workflow, radiation detectors and with corresponding image processing and acquisition settings (profiles). Report generator 34 identifies a workflow and image processing function in response to an identified sequence of steps. In one embodiment, a lookup table is used associating step sequences with a workflow type.

Image quality profiles comprise a set of image processing parameters (e.g. settings which are a combination of organ program parameters and image quality configuration parameters) that are pre-validated to provide optimal image quality for an image processing function with a particular set of X-ray radiation detectors and type of image acquisition (e.g. workflow being executed by a user), for example. When system 10 is operating in quality analysis function mode, a user workflow is identified by parsing user actions and a corresponding subset of image quality profiles is selected from a lookup table. System 10 automatically identifies poor image quality and prompts a user that image quality may be deficient e.g. by comparison with template reference images of an anatomical region of interest (ROI) concerned or by detecting, common artifacts, banding, poor luminance range, or monochrome areas, for example. Artifact detection is performed by object edge detection using a known edge detection function based on adjacent pixel luminance transition occurring and by object shape matching and comparison with template features (e.g. spaced bands) using scaling, rotation and translation operations.

Figure 5:
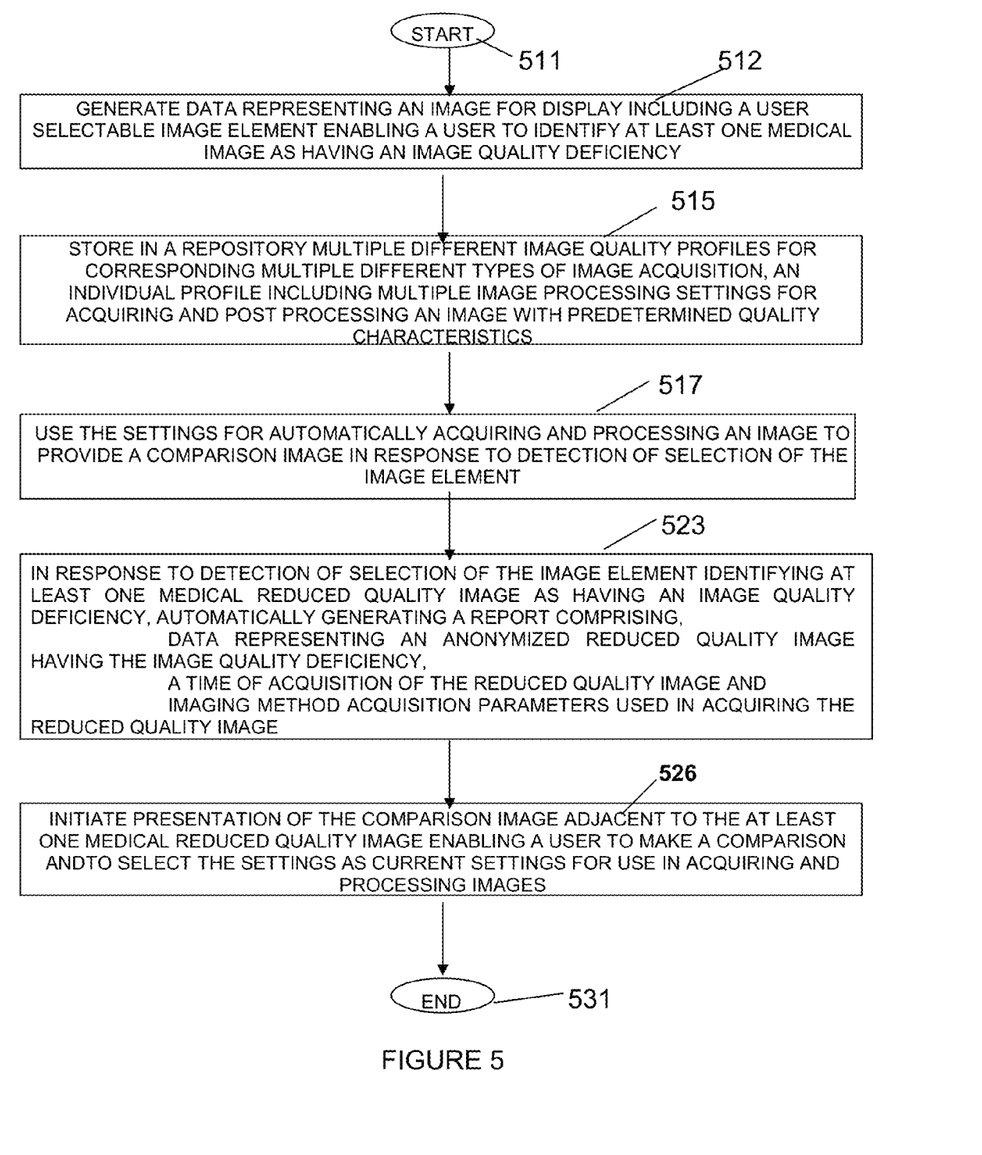
FIG. 5 shows a flowchart of a process used by a medical image quality reporting and monitoring system for use in a medical imaging system, according to invention principles.

FIG. 5 shows a flowchart of a process used by medical image quality reporting and monitoring system 10 (FIG. 1) for use in a medical imaging system. In step 512 following the start at step 511 system 10 employs medical image computer 30 including display processor 15 for generating data representing an image for display including a user selectable image element enabling a user to identify at least one medical image as having an image quality deficiency. Display 19 presents the image. In step 515 computer 30 stores in repository 17 multiple different image quality profiles for corresponding multiple different types of image acquisition. An individual profile includes multiple image processing settings for acquiring and post processing an image with predetermined quality characteristics. Image processor 29 in step 517 uses the settings for automatically acquiring and processing an image to provide a comparison image in response to detection of selection of the image element. Image processor 29 anonymizes a reduced quality image by removing patient identification data associated with the reduced quality image and exporting data representing the anonymized image to a predetermined directory on the imaging system.

In step 523, report generator 34, in response to detection of selection of the image element identifying at least one medical reduced quality image as having an image quality deficiency, automatically generates a report. The report comprises, data representing an anonymized reduced quality image having the image quality deficiency, a time of acquisition of the reduced quality image and imaging system acquisition settings used in acquiring the reduced quality image. In one embodiment, the report comprises data representing multiple anonymized reduced quality images displayed on one or more display screens at the time of user selection of the image element. The report also comprises a record of a sequence of user interface actions occurring preceding and related to acquisition of the reduced quality image and a problem description and method configuration settings. In step 526, image processor 29 initiates presentation of the comparison image adjacent to the at least one medical reduced quality image enabling a user to make a comparison and enables a user to select the settings as current settings for use in acquiring and processing images. The process of FIG. 5 terminates at step 531.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface comprises one or more display elements enabling user interaction with a processor or other device. A computer is a hardware element comprising a controller, logic device, programmed logic array or other processing device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system enables a user to express dissatisfaction with an acquired image via simple button press on a displayed image and in response, generates a comparison image using predetermined optimized image acquisition and post-processing settings for side by side comparison with the original image enabling a user to compare images and select the predetermined settings. Further, the processes and applications may, in alternative embodiments, be located on one or more (e.g., distributed) processing devices on a network linking the units FIG. 1. Any of the functions and steps provided in FIGS. 1-5 may be implemented in hardware, software or a combination of both. No claim element herein is to be construed under the provisions of 35 U.S.C. 112, sixth paragraph, unless the element is expressly recited using the phrase "means for."

What is claimed is:

1. A medical image quality reporting and monitoring system for use in a medical imaging system, comprising:
   a medical image computer including,
      a display processor configured to generate data representing an image for display including a user selectable image element enabling a user to identify at least one medical image as having an image quality deficiency and
      a display configured to present said image;
   a repository of a plurality of different pre-validated image quality profiles for a corresponding plurality of different types of image acquisition, an individual profile including a plurality of predetermined image processing settings and user-executed workflow actions for acquiring and post processing an image with optimal image quality characteristics;
   an image processor configured to
      anonymize a reduced quality image by removing patient identification data associated with said reduced quality image; and
      use said pre-validated image quality profiles for automatically acquiring and processing an image to provide a comparison image in response to detection of selection of said user selectable image element; and
   a report generator configured to, in response to detection of selection of said user selectable image element, identify at least one medical reduced quality image as having a particular image quality deficiency, automatically generate a report comprising,
      data representing an anonymized reduced quality image having said particular image quality deficiency,
      a time of acquisition of said reduced quality image,
      imaging system acquisition settings used in acquiring said reduced quality image, and
      a record of a sequence of user interface actions occurring preceding and related to acquisition of said reduced quality image.

2. The system according to claim 1, wherein
   said report comprises a problem description and system configuration settings.

3. The system according to claim 2, wherein
   said report comprises data representing a plurality of anonymized reduced quality images displayed on one or more display screens at the time of user selection of said user selectable image element.

4. The system according to claim 1, the image processor further configured to export data representing the anonymized reduced quality image to a predetermined directory on the imaging system.

5. The system according to claim 1, wherein
   said image processor initiates presentation of said comparison image adjacent to said at least one medical reduced quality image enabling a user to make a comparison.

6. The system according to claim 1, wherein
said image processor enables a user to select said settings as current settings for use in acquiring and processing images.

7. A medical image quality reporting and monitoring system for use in a medical imaging system, comprising:
a medical image computer including, a display processor for generating data representing an image for display including a user selectable image element enabling a user to identify at least one medical image as having an image quality deficiency and
a display for presenting said image a repository of a plurality of different pre-validated image quality profiles for a corresponding plurality of different types of image acquisition, an individual profile including a plurality of predetermined image processing settings and user-executed workflow actions for acquiring and post processing an image with optimal image quality characteristics: and an image processor configured to anonymize a reduced quality image by removing patient identification data associated with said reduced quality image and for using said pre-validated image quality profiles for automatically acquiring and processing an image to provide a comparison image in response to detection of selection of said user selectable image element and a report generator for, in response to detection of selection of said image element identifying at least one medical reduced quality image as having a particular image quality deficiency, automatically generating a report comprising, data representing an anonymized reduced quality image having
said image quality deficiency, a time of acquisition of said reduced quality image and
imaging system acquisition settings used in acquiring said reduced quality image and a record of a sequence of user interface actions occurring preceding and related to acquisition of said reduced quality image.

8. The system according to claim 7, wherein
said image processor initiates presentation of said comparison image adjacent to said at least one medical reduced quality image enabling a user to make a comparison.

9. The system according to claim 7, wherein
said image processor enables a user to select said settings as current settings for use in acquiring and processing images.

10. A method of medical image quality reporting and monitoring for use in a medical imaging system, comprising the activities of:
pre-validating image quality profiles for a corresponding plurality of different types of image acquisition, an individual profile including a plurality of predetermined image processing settings and user-executed workflow actions for acquiring and post processing an image with optimal image quality characteristics;
employing at least one computer for,
generating data representing an image for display including a user selectable image element enabling a user to identify at least one medical image as having an image quality deficiency;
anonymizing a reduced quality image by removing patient identification data associated with said reduced quality image;
in response to detection of selection of said image element, identifying at least one medical reduced quality image as having a particular image quality deficiency, automatically generating a report comprising,
data representing an anonymized reduced quality image having said particular image quality deficiency,
a time of acquisition of said reduced quality image,
imaging method acquisition settings used in acquiring said reduced quality image, and
a record of a sequence of user interface actions occurring preceding and related to acquisition of said reduced quality image; and
using said pre-validated image quality profiles for automatically acquiring and processing an image to provide a comparison image in response to detection of selection of said user selectable image element.

11. The method according to claim 10, wherein
said report comprises a problem description and method configuration settings.

12. A medical image quality reporting and monitoring method for use in medical imaging, comprising the activities of:
employing at least computer for,
generating data representing an image for display including a user selectable image element enabling a user to identify at least one medical image as having an image quality deficiency storing in a repository a plurality of different pre-validated image quality profiles for a corresponding plurality of different types of image acquisition, an individual profile including a plurality of predetermined image processing settings and user-executed workflow actions for acquiring and post processing an image with optimal image quality characteristics
anonymizing a reduced quality image by removing patient identification data associated with said reduced quality image; and
using said predetermined image processing settings and user-executed workflow actions for automatically acquiring and processing an image to provide a comparison image for user review and in response to detection of selection of said user selectable image element
in response to detection of selection of said image element identifying at least one medical reduced quality image as having a particular image quality deficiency, automatically generating a report comprising, data representing an anonymized reduced quality image having said particular image quality deficiency,
a time of acquisition of said reduced quality image and
imaging method acquisition settings used in acquiring said reduced
quality image and a record of a sequence of user interface actions occurring preceding and related to acquisition of said reduced quality image.

13. The method according to claim 12, including the activity of, initiating presentation of said comparison image adjacent to said at least one medical reduced quality image enabling a user to make a comparison.

14. The method according to claim 12, including the activity of
enabling a user to select said settings as current settings for use in acquiring and processing images.

15. The system of claim 2 wherein said settings comprise two or more of a pixel shifting algorithm, an autopixelshift threshold, a vessel representation, a number of frames used to perform mask averaging for noise reduction, a pixel resolution, a pixel depth, an autowindow activation and range, a Gamma correction value, a vessel contrast, and a catheter contrast.

\* \* \* \* \*